United States Patent [19]

Abeles

[11] Patent Number: 5,207,909
[45] Date of Patent: May 4, 1993

[54] PLASMA POLYMER MEMBRANE (C-2564)

[75] Inventor: Benjamin Abeles, Princeton, N.J.

[73] Assignee: Exxon Research and Engineering Company, Florham Park, N.J.

[21] Appl. No.: 857,200

[22] Filed: Mar. 25, 1992

[51] Int. Cl.$^5$ .............................................. B01D 39/00
[52] U.S. Cl. ................................... 210/500.27; 55/16; 264/22
[58] Field of Search ............................ 521/61; 55/16; 210/500.27; 264/22

[56] References Cited

U.S. PATENT DOCUMENTS 4,876,294 10/1989 Shriver et al. ..................... 523/139
4,974,659 12/1990 Shriver et al. ..................... 521/139

OTHER PUBLICATIONS

Hidetoshi Kita, Taro Sakamoto, Kazuhiro Tanaka and Ken-Ichi Okomoto, Polymer Bulletin 20, 349-354 (1988).

N. Inagaki, N. Kobayashi and M. Matsushima, J. Membr. Science 38, 85 (1988).

Mitsuyasu Kawakami, Yukinori Yamashita, Masakazu Iwamoto and Shuichi Kagawa, J. Membr. Science 19, 249 (1984).

A. E. Stancell and A. T. Spencer, J. Appl. Polymer Science 16, 1505 (1972).

Primary Examiner—Morton Foelak
Attorney, Agent, or Firm—Ronald D. Hantman

[57] ABSTRACT

The present invention is a membrane for separating aromatics from feeds which are mixtures of aromatics and saturates and for separating saturated linear hydrocarbons from feeds which are mixtures of saturated linear and saturated branched hydrocarbons. The membrane is a plasma polymer formed from plasma polymerizing monomers. In a preferred embodiment, the membrane is a plasma polymer film formed from plasma polymerizing the monomer 2,4 pentane dione.

9 Claims, 6 Drawing Sheets

PLASMA POLYMER MEMBRANE (C-2564)

BACKGROUND

The present invention relates to plasma polymer membrane for the separation of one component from an organic feed. In a preferred embodiment the separation is aromatics from saturates.

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e., aromatic, unsaturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g., aromatic and/or olefins from gasoline boiling range mixtures, by the selective permeation of the aromatic through certain non-porous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

The principle in the separation of aromatics and saturates in the above polymer membranes is that in a feed consisting of a mixture of aromatics and saturates the aromatic molecules are preferably soluble in the membrane compared to the saturated molecules and, as a result, the aromatics are preferentially removed at the permeate side of the membrane. In the case of polyurethane membranes, the polymer consists of a hard block-soft block copolymer. The soft blocks preferentially sorb aromatics while the hard blocks act as effective crosslink to provide the mechanical stability for the membrane. The soft blocks usually consist of polyethylene adipate oligamers in which the carbonyl groups are responsible for the preferential sorbtion of the aromatics.

In addition to its solubility of the molecule, the diffusion coefficient also plays a role in determining the selectivity of the membrane. This is because the flux $F_i$ of molecular species i through the membrane is given by:

$$F_i = D_i(dC_i/dx)$$

where $D_i$ is the diffusion coefficient, $C_i$ is the concentration in the membrane and $dC_i/dx$ is the concentration gradient. Thus the flux of the molecules is governed both by the solubility as well as by the diffusion coefficient.

SUMMARY OF THE PRESENT INVENTION

The present invention is a membrane for separating at least one component from an organic feed. In a preferred embodiment, the feed is a mixture of aromatics and non-aromatics. In another embodiment, the membrane of the present invention is used for separating linear hydrocarbons from feeds which are mixtures of linear and branched hydrocarbons. The membrane of the present invention is a plasma polymer formed from plasma polymerizing monomers. In a preferred embodiment, the membrane is a plasma polymer film formed from plasma polymerizing the monomer 2,4 pentane dione.

DESCRIPTION OF THE PREFERRED EMBODIMENT

Figure 1:
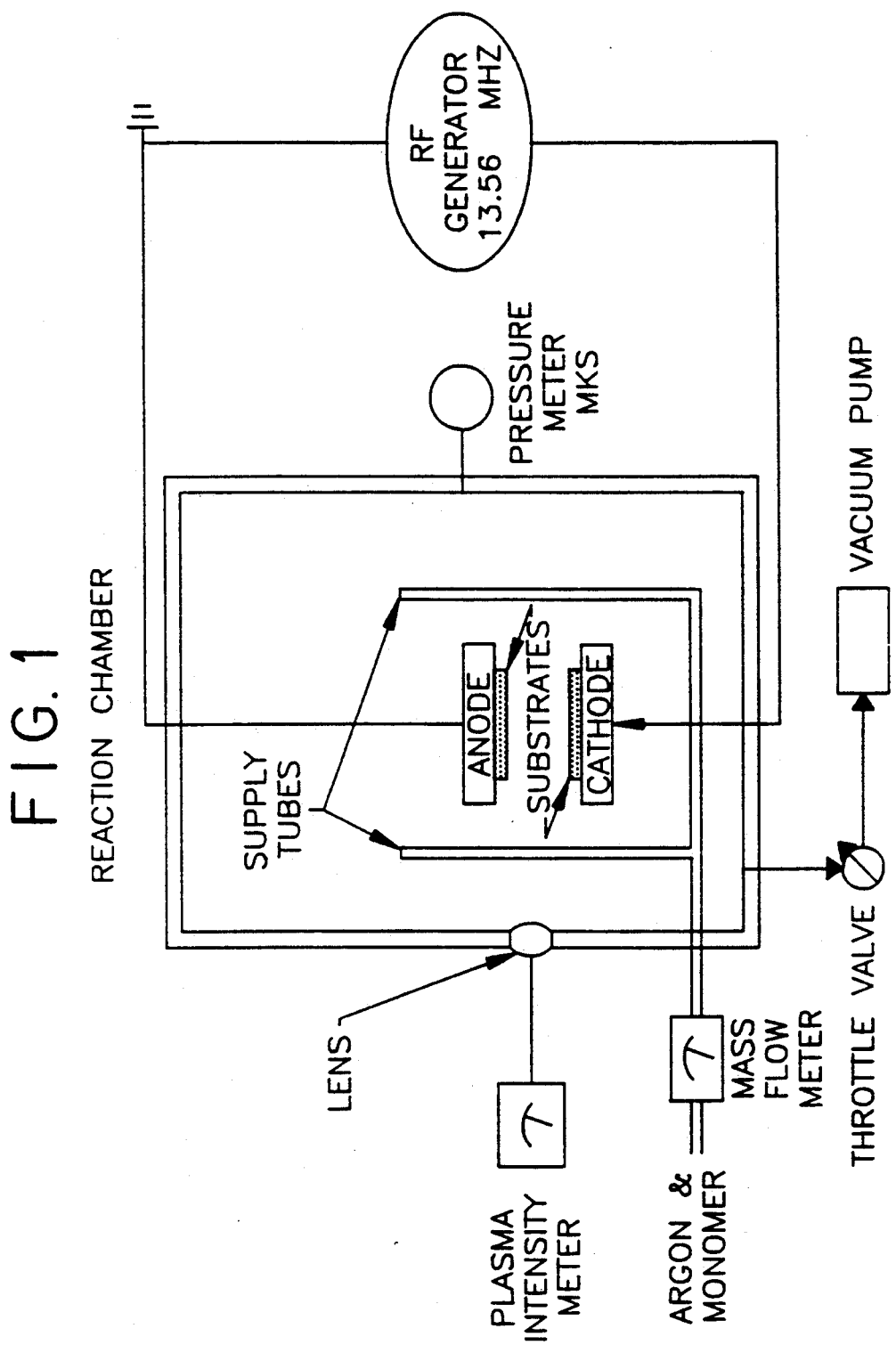
FIG. 1 shows a schematic diagram of capacitive plasma CVD reactor used for depositing the polymer membrane films.

For descriptive purposes, the plasma polymerized membrane of the present invention shall be illustrated and described for separating aromatics from mixtures of aromatic and non-aromatics. The membrane also shall be illustrated and described for separating linear hydrocarbons from mixtures of linear and branched hydrocarbons. The plasma membrane of the present invention separate the mixtures by the solution-diffusion mechanism.

The membranes of the present invention are prepared by plasma polymerization. The process of plasma polymerization differs fundamentally from the conventional free radical polymerization by which the polymers in the patents cited above were made. In the conventional polymerization process polymer chains grow by repeated addition of monomers where the monomers retain their original identify in the chain. In contrast in plasma polymerization the plasma discharge breaks up the precursor monomer into a wide range of molecular weight charged and neutral fragments which are then reconstituted on the substrate as a film or in the gas phase as a powder. The resulting polymer is strongly crosslinked and its structure bears little resemblance to that of the precursor monomer. Because plasma polymer films are so strongly crosslinked only small molecules are soluble in them. Hence membranes made by plasma polymerization of organic or organosilicon monomers have been used extensively in the past only for separation of small molecules such as $N_2$, $O_2$, $CO_2$, $H_2$, $CH_4$, etc. (Hidetoshi Kita, Taro Sakamoto, Kazuhiro Tanaka and Ken-Ichi Okomoto, Polymer Bulletin 20, 349-354 (1988); N. Inagaki, N. Kobayashi and M. Matsushima, J. Membr. Science 38, 85 (1988); Mitsuyasu Kawakami, Yukinori Yamashita, Masakazu Iwamoto and Shuichi Kagawa J. Membr. Science 19, 249 (1984); A. E. Stancell and A. T. Spencer J. Appl. Polymer Science 16, 1505 (1972)) and desalination of water, and ethanol water separation. These membranes work on the basis of reverse osmosis, in which separation is achieved primarily by molecular sieving.

The plasma polymer membranes of the present invention are based on the solution-diffusion mechanism just as the conventional membranes disclosed in the patents cited above. To achieve plasma polymer membranes with such properties two conditions must be satisfied (1) the polymer must contain functional groups which have a relatively larger attractive energy for aromatics than for saturates (2) the polymer must be sufficiently loosely crosslinked to permit permeation of large hydrocarbon molecules. The first condition can be achieved by using precursors with functional groups that are strongly polar such as C=O, C—Cl, C—F, etc. To achieve the second condition the plasma discharge energy must be sufficiently low not to cause excessive crosslinking and to avoid fragmentation of the desirable functional groups, but not so low that the network would become soluble in the feed solvents. This places rather narrow limits on the choice of the precursor molecules and on the plasma discharge conditions.

The plasma polymer membrane of the present invention was prepared by plasma polymerizing the monomer 2,4 pentane dione. This particular monomer was used because carbonyl groups are strongly polar and so are expected to have a large attractive energy with respect to aromatic molecules. Furthermore, 2,4 pentane dione is similar in structure to the polyethylene adipate oligomer used as a building block of the soft segment block in polyurethane membranes. Finally 2,4 pentane dione has a sufficiently large vapor pressure at room temperature required for the plasma discharge.

Figure 2:
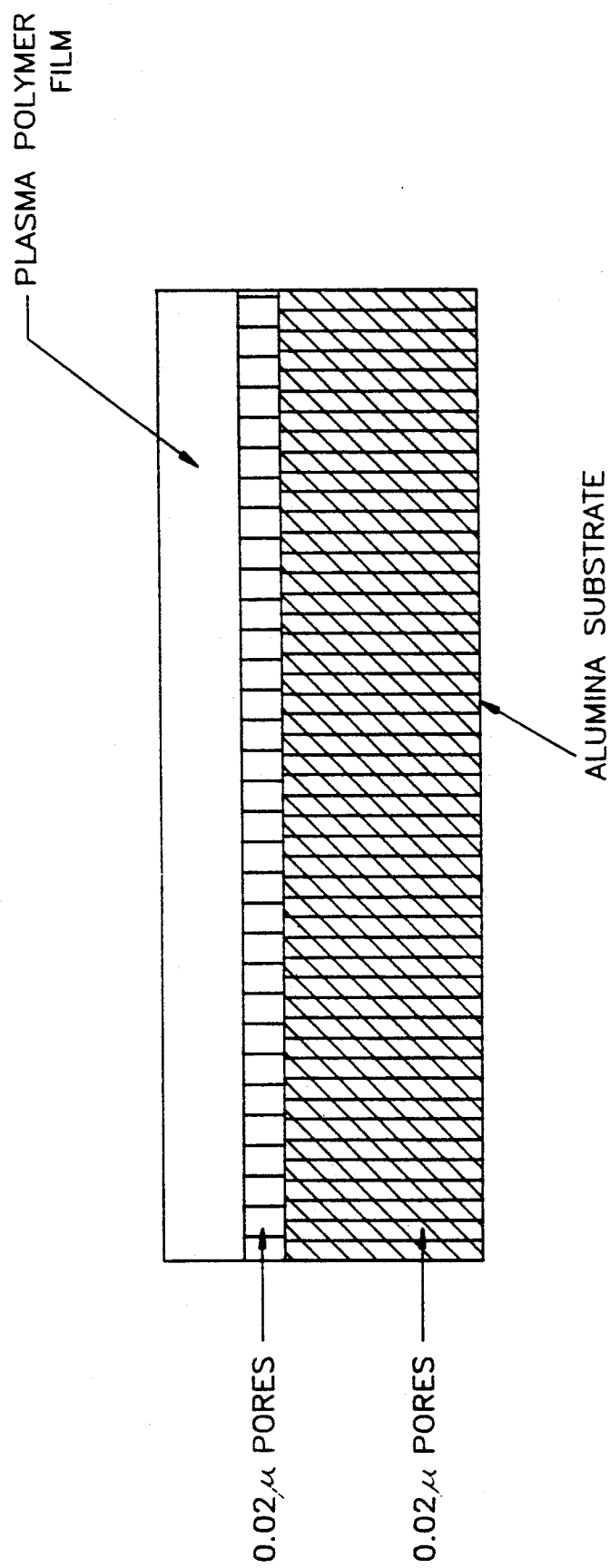
FIG. 2 shows the structure of plasma polymer membrane.

The plasma polymer films were deposited in a RF capacitive reactor (see FIG. 1) using the monomer 2,4 pentane dione diluted with Ar. The substrates used for the membranes were alumina discs with the trade name "Anapore" from Anotec. The discs were 25 mm in diameter and had 0.02 μm pores. The alumina substrates were placed on both the anode and cathode electrodes of the plasma reactor. Films deposited on cathode are referred to as cathodic, and those on the anode as anodic. FIG. 2 shows the structure of the plasma polymer membrane which was used for the permeation measurements. The optimum film deposition conditions are listed in Table 1.

TABLE 1

| Deposition Parameters | |
|---|---|
| Argon | 21 cc/min (STP) |
| Pentane Dione | 4 cc/min (STP) |
| Pressure | 230 mtorr |
| RF Power | 28-32 Watt, 13.56 MHz |

TABLE 1-continued

| Deposition Parameters | |
|---|---|
| Deposition Rate | 0.6 Å/sec |

Figure 3:
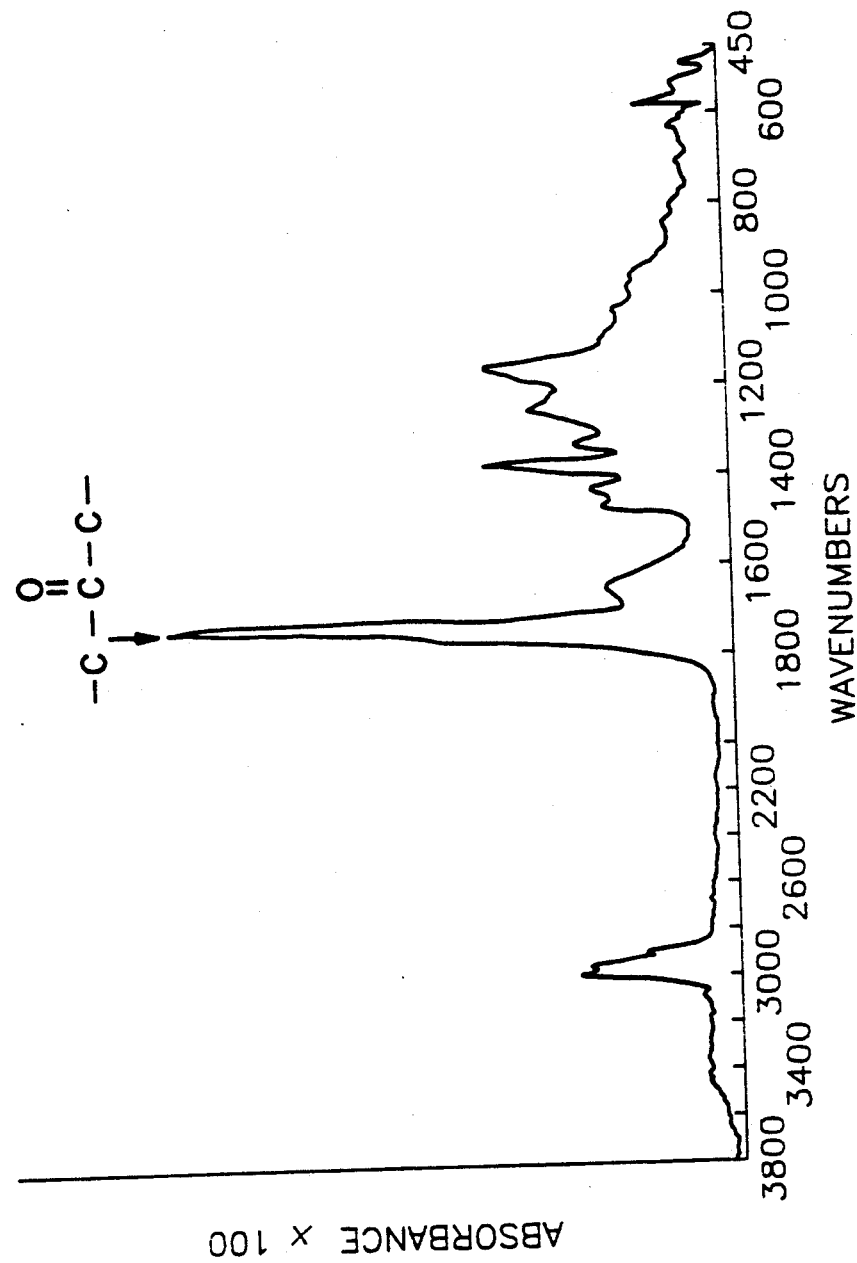
FIG. 3 shows an IR transmission spectrum of 2 μm thick plasma polymer film on KBr substrate. The characteristic carbonyl vibrational mode at 1700 cm$^{-1}$ is indicated in the figure.

FIG. 3 shows a typical IR spectrum of the polymer. The strong absorption peak at 1720 $cm^{-1}$ corresponds to the carbonyl group.

Figure 4A:
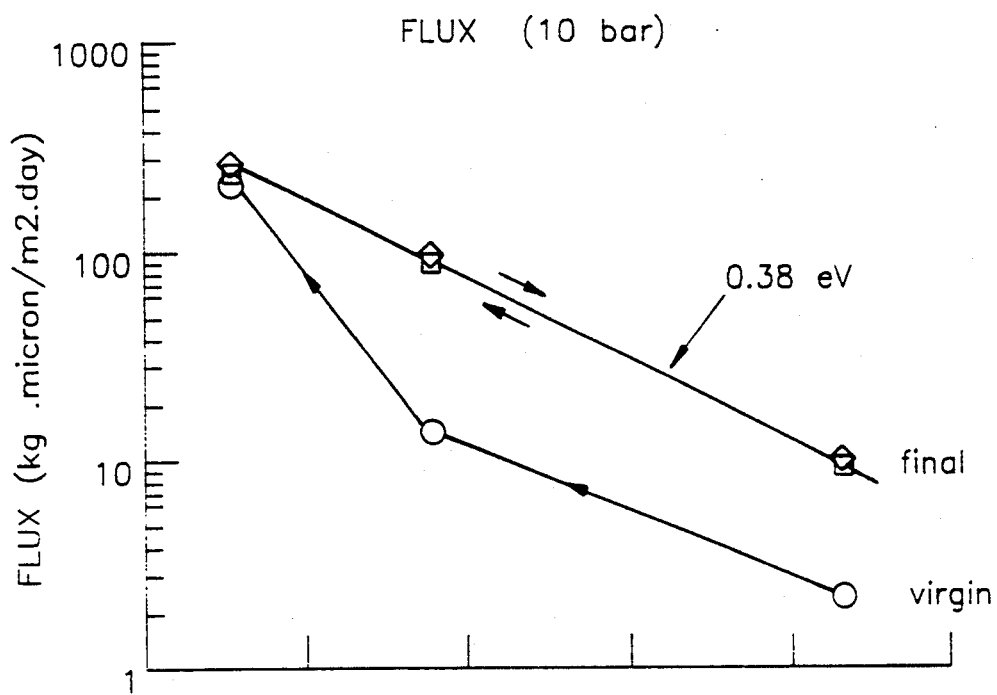
FIGS. 4A and 4B show the temperature dependence of flux and selectivity, respectively, of 1:1 mixture by weight of toluene and n-octane permeating through a cathodic plasma polymer film. Measurements were made at 10 bar inlet pressure. Virgin film undergoes irreversible change on initial heating while in contact with the hydrocarbon feed.
Figure 4B:
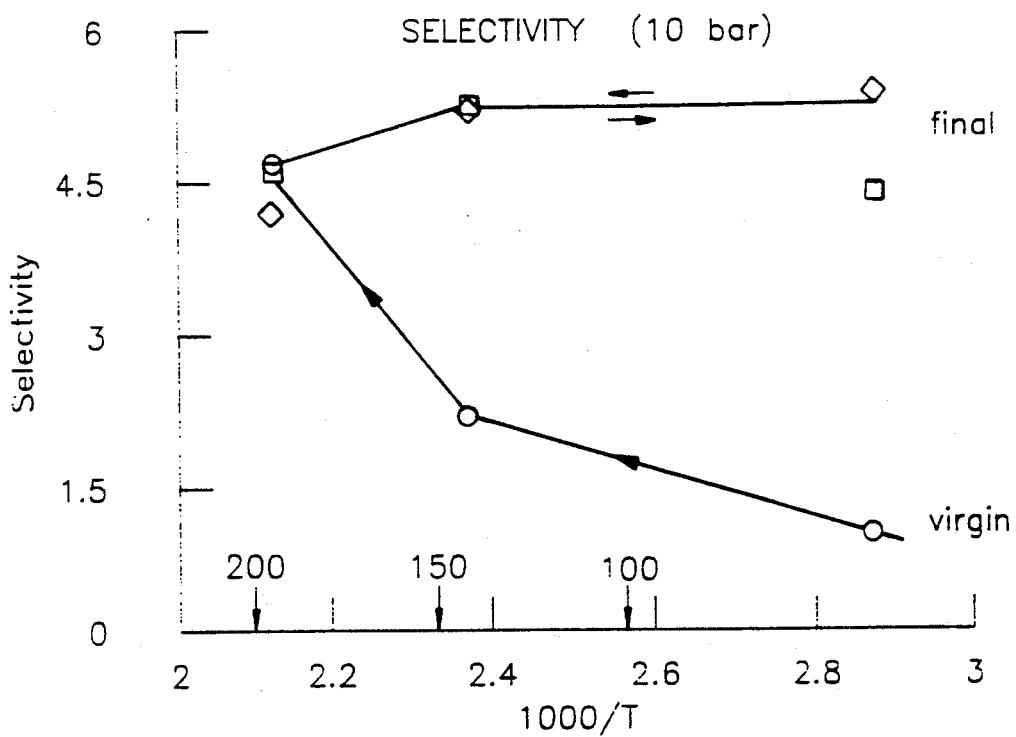

Permeation and selectivity of mixtures of toluene, n-octane and isooctane through the plasma membranes were determined by pervaporation. Initially at room temperature the membranes had a very low permeability and selectivity. Only after heating the membrane to 200° C. under operating conditions did the flux and selectivity rise and reach their final steady state values. During the forming process, the feed dissolves and removes molecules that are only weakly crosslinked, thereby producing a looser network and consequently increasing the permeability of the polymer. After the initial forming process the membranes remained stable under operating conditions over many days and could be temperature cycled without any hysteresis. The forming process is illustrated in FIG. 4 for a 1000 Å cathodic plasma polymer film for the case of a mixture 1:1 by weight of toluene/n-octane.

Figure 5A:
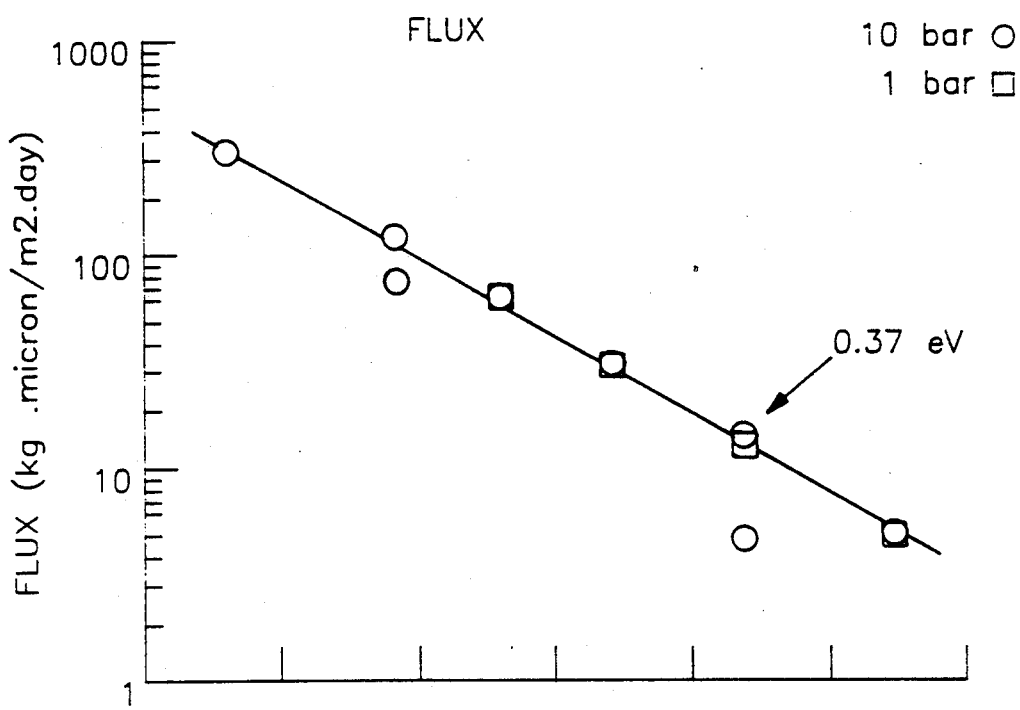
FIGS. 5A and 5B show the temperature dependence of flux and selectivity, respectively, of 1:1 mixture weight of toluene and i-octane for the same film as in FIG. 4. Measurements made at 1 and 10 bar inlet pressures.
Figure 5B:
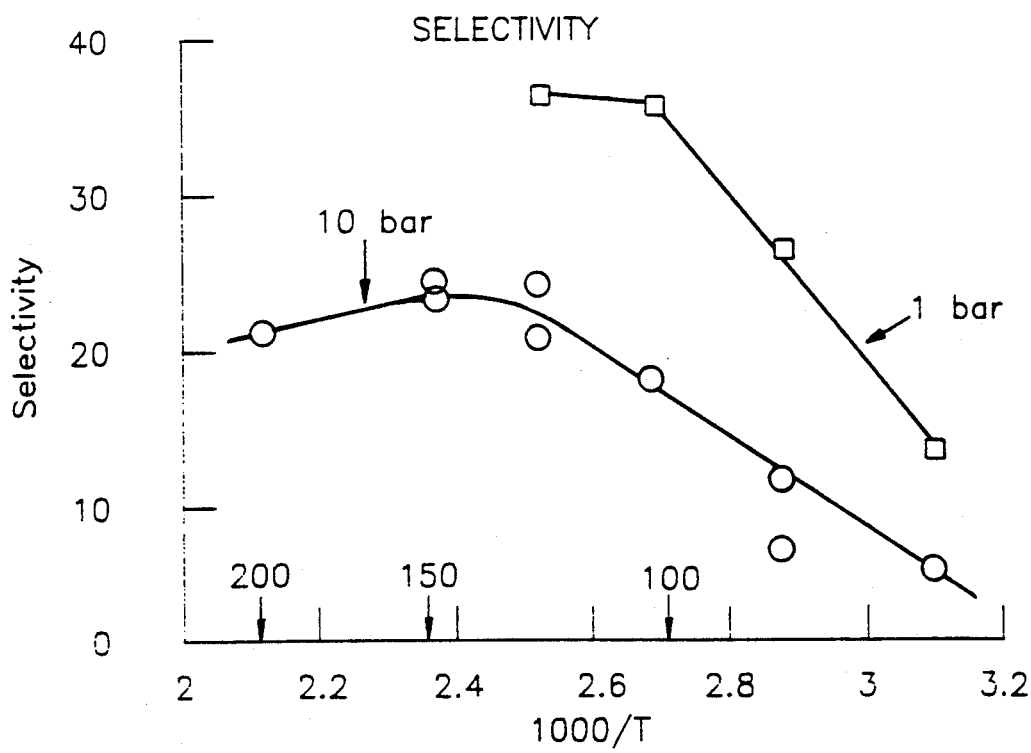
Figure 6A:
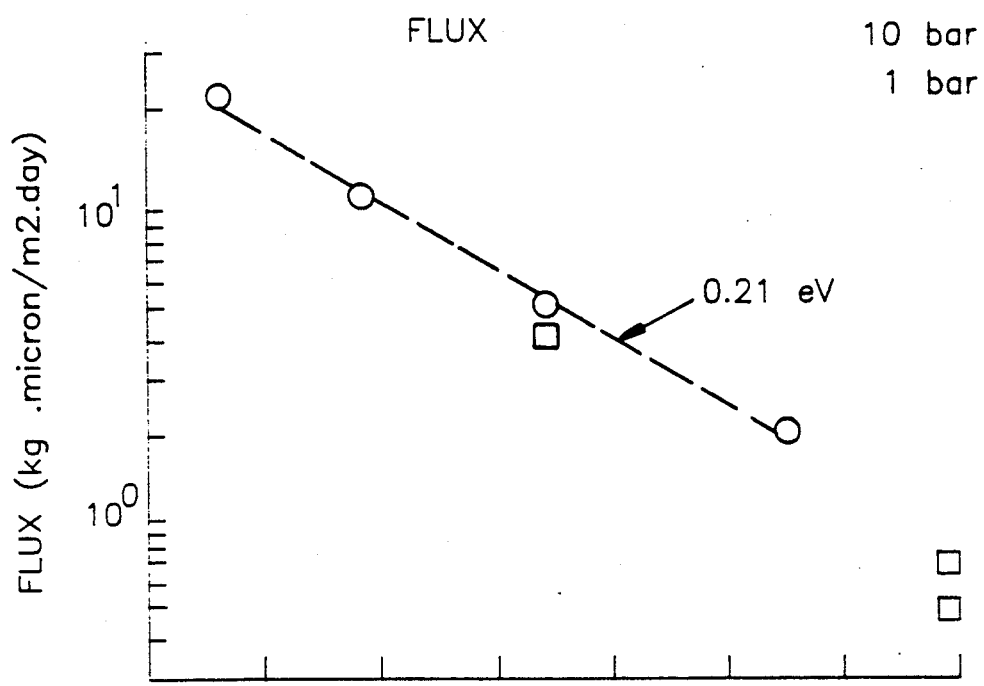
FIGS. 6A and 6B show the temperature dependence of flux and selectivity, respectively, of 1:1 mixture by weight of n-octane and i-octane for the same film as in FIG. 4. Measurements made at 1 and 10 bar inlet pressures.
Figure 6B:
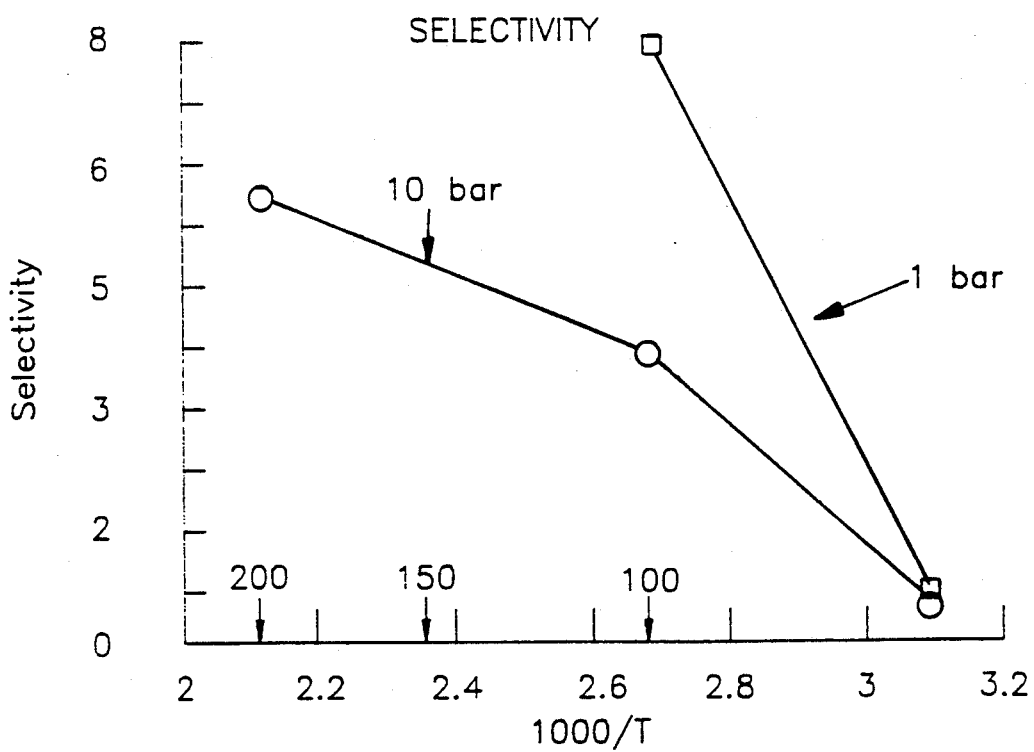

The flux through the membrane was found to be independent of hydraulic pressure. This finding, illustrated for the case of separating toluene from toluene/i-octane in FIG. 5 and separating n-octane from n-octane/isooctane in FIG. 6 indicated that transport through the membrane is diffusive rather than by reverse osmosis. The fact that the selectivity decreases with increasing hydraulic pressure is believed to be the result of small pinholes. Flow through pinholes is proportional to the hydraulic pressure and has no selectivity. Thus at high hydraulic pressures the flow through pinholes becomes more important and thus reduces the selectivity.

The separation for a mixture toluene/i-octane is even larger then for the toluene/n-octane feed. This is demonstrated in FIG. 5 for a feed of 1:1 toluene/i-octane where the selectivity for toluene at 200° C. and pressure of 10 barr is 20. This enhanced selectivity may be in part due to a smaller solubility in the membrane of i-octane compared to n-octane. However, the major effect is likely due to the diffusion coefficient for i-octane being smaller then for n-octane because the former molecule is branched while the latter is linear and thus finds it easier to diffuse through the polymer network. The fact that n-octane diffuses faster then i-octane is demonstrated directly in FIG. 5 for a mixture of 1:1 n-octane/i-octane which shows a selectivity of 6 for n-octane.

What is claimed is:

1. A membrane for separating at least one component selected from the group consisting of an aromatic and linear hydrocarbons, from organic feeds comprising a plasma polymer formed from plasma polymerizing monomers which contain functional groups selected from the group consisting of C—Cl, C—F, and C=O, having polarity so as to separate said component from said feed.

2. The membrane of claim 1 wherein said component is an aromatic and said feeds are a mixture of aromatics and saturates and said membrane includes a plasma polymer formed from plasma polymerizing the monomer 2-4 pentane dione.

3. The membrane of claim 1 wherein said component is an aromatic and said feeds are a mixture of aromatics and saturates.

4. The membrane of claim 1 wherein said component is a saturated linear hydrocarbon and said feeds are mixtures of saturated linear and saturated branched hydrocarbons and said membrane includes a plasma polymer formed from plasma polymerizing monomers which contain functional groups that have a larger attractive energy for linears than for branched.

5. The membrane of claim 1 wherein said component is a linear hydrocarbon and said feeds are mixtures of saturated linear and saturated branched hydrocarbons and said membrane includes a plasma polymer formed from plasma polymerizing the monomer 2-4 pentane dione.

6. The membrane of claim 1 wherein said component is a saturated linear hydrocarbon and said feeds are mixtures of saturated linear and branched linear hydrocarbons.

7. A membrane of claim 1 wherein said component is a saturated linear hydrocarbon and said feeds are mixtures of saturated linear and saturated branched hydrocarbons, and said membrane includes a plasma polymer in which the diffusion coefficient for the linear molecules is larger then for the branched molecules.

8. The plasma polymerized membrane of claim 1 wherein said membrane has its permeability and selectivity increased by the forming process which consists of pervaporating toluene through the membrane.

9. The plasma polymerized membrane of claim 1 wherein said membrane has its permeability and selectivity increased by the forming process in which the membrane is placed for several hours in toluene.

* * * * *